United States Patent

Tamura et al.

[11] Patent Number: 5,817,892
[45] Date of Patent: Oct. 6, 1998

[54] PROCESS FOR PRODUCING UNSATURATED ALCOHOL

[75] Inventors: Hiroyuki Tamura; Hideo Tahara; Yoshinori Mitsuda; Yasuyuki Hattori, all of Wakayama, Japan

[73] Assignee: Kao Corporation, Tokyo, Japan

[21] Appl. No.: 915,594

[22] Filed: Aug. 21, 1997

[30] Foreign Application Priority Data

Jun. 9, 1996 [JP] Japan .................................. 8-236219

[51] Int. Cl.$^6$ ................................................. C07C 29/136
[52] U.S. Cl. ........................ 568/885; 568/852; 568/909.5
[58] Field of Search ................................ 568/885, 909.5, 568/852

[56] References Cited

U.S. PATENT DOCUMENTS 5,475,160 12/1995 Singleton ................................. 568/864
5,478,789 12/1995 Hattori ..................................... 502/244

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

A process for producing an unsaturated alcohol wherein the catalytic activity and the capability of maintaining double bond are sustained for a long time and side-reactions are suppressed. An unsaturated alcohol is obtained by hydrogenating an alkyl or alkenyl ester of an unsaturated fatty acid or a triglyceride having a long-chain aliphatic unsaturated hydrocarbon group in the presence of a catalytic composition which is a composite metal oxide consisting of (a) zinc oxide and (b) oxide(s) of at least one metal selected from the group consisting of the elements of the group 3A in the periodic table and having a weight ratio of (a)/(b) of from 1/0.01 to 1/1.2.

4 Claims, No Drawings

PROCESS FOR PRODUCING UNSATURATED ALCOHOL

FIELD OF THE INVENTION

This invention relates to a process for producing an unsaturated alcohol. More particularly, it relates to a process for producing an unsaturated alcohol at a high yield and a high selectivity by hydrogenating an ester of an unsaturated fatty acid or a triglyceride in the presence of a catalyst.

BACKGROUND OF THE INVENTION

There have been reported a number of processes for producing unsaturated alcohols by hydrogenating unsaturated aldehydes, unsaturated fatty acids or esters thereof in the presence of various catalysts. For example, JP-B-45-2562 proposes a method for the continuous hydrogenation in the presence of a zinc oxide/chromium oxide catalyst which is characterized in that the catalyst employed is one having been treated at a high temperature of 400° to 1,000° C., preferably 500° to 900° C., in a reductive atmosphere. Further, JP-B-54-36731 proposes a fixed bed reaction system with the use of a four- or five-component catalyst composed of zinc oxide and/or cadmium oxide, aluminum oxide, chromium oxide and barium oxide (The term "JP-B" as used herein means an "examined Japanese patent publication").

However, the above-mentioned methods are not preferable from the viewpoint of environment protection, since chromium oxide and cadmium oxide are employed therein. Moreover, these methods are not always satisfactory from the viewpoints of activity and selectivity too.

Also, it has been proposed for a long time to use an iron/zinc composite oxide catalyst in the production of unsaturated alcohols. For example, Kogyo Kagaku Zasshi (J. Industrial Chem.), 44 (6), 740 (1941) proposes a composite catalyst consisting of iron oxide/zinc oxide (95/5). However, this catalyst is unsatisfactory in the catalytic activity and the selectivity regarding capability of maintaining carbon-carbon double bond (hereinafter referred to simply as "capability of maintaining double bond").

To solve this problem, JP-A-59-106431 discloses a process for producing unsaturated alcohols wherein the catalytic activity and the selectivity regarding capability of maintaining double bond have been improved by using a three-component catalyst consisting of iron oxide, zinc oxide and zirconium oxide (The term "JP-A" as used herein means an "unexamined published Japanese patent application"). When used in the reaction repeatedly, however, the three-component catalyst consisting of iron oxide, zinc oxide and zirconium oxide undergoes morphological changes due to the reduction of iron oxide and thus saturated alcohols are formed as by-products in an elevated amount. That is to say, there arises a new problem that the selectivity regarding the capability of maintaining double bond cannot be sustained in a desirable state for a long time.

SUMMARY OF THE INVENTION

Accordingly, an object of the present invention is to provide a process for producing an unsaturated alcohol at a high yield and a high selectivity while sustaining a high catalytic activity and a good capability of maintaining double bond for a long time and suppressing side-reactions.

Under these circumstances, the present inventors have conducted extensive studies. As a result, they have found out that the above-mentioned problems can be solved by using a catalyst of a highly selected composition. Moreover, they have surprisingly found out that the unsaturated alcohol obtained by using the above-mentioned catalyst is scarcely accompanied by the isomerization of the double bond in the starting unsaturated compound, thus completing the present invention.

Accordingly, the present invention provides a process for producing an unsaturated alcohol which comprises hydrogenating an alkyl or alkenyl ester of an unsaturated fatty acid or a triglyceride having a long-chain aliphatic unsaturated hydrocarbon group in the presence of a catalytic composition which is a composite metal oxide consisting of (a) zinc oxide and (b) oxide(s) of at least one metal selected from the group consisting of the elements of the group 3A in the periodic table and having a weight ratio of (a)/(b) of from 1/0.01 to 1/1.2.

DETAILED DESCRIPTION OF THE INVENTION

Now, the embodiments of the present invention are described in detail.

The elements of the group 3A in the periodic table to be used in the present invention include Sc, Y, lanthanoid elements (La, Ce, Pr, Nd, Pm, Sm, Eu, Gd, Tb, Dy, Ho, Er, Tm, Yb and Lu) and actinoid elements (Ac, Th, Pa, U, Np, Pu, Am, Cm, Bk, Cf, Es, Fm, Md, No and Lr). Among these elements, Y, La, Ce and Th are preferred.

The term "periodic table" as used herein means the one described in "Kagaku Binran: Kisohen II (A Handbook of Chemistry: Fundamental Section II) ", 4th ed., edited by The Japan Chemical Society, Maruzen, Sep. 30, 1993).

The catalytic composition according to the present invention, which is a composite metal oxide consisting of (a) zinc oxide and (b) oxide(s) of metal(s) of the group 3A in the periodic table, may contain any well-known catalyst carrier, so long as the effects of the present invention are not worsened thereby.

The catalytic composition according to the present invention may be produced by any well-known method without restriction. When no carrier is employed, for example, a catalytic composition precursor is first prepared by co-precipitating water soluble salt(s) of at least one element selected from the group consisting of the elements of the group 3A in periodic table together with a water soluble zinc salt, impregnating a sparingly water-soluble zinc compound such as zinc oxide, zinc hydroxide or zinc carbonate with water soluble salt(s) of at least one element selected from the group consisting of the elements of the group 3A in periodic table, or precipitating such a sparingly water-soluble zinc compound with water soluble salt(s) of at least one element selected from the group consisting of the elements of the group 3A in periodic table. Then the catalytic composition precursor is calcined to thereby produce the catalytic composition. Alternatively, when the carrier is employed, a catalytic composition precursor may be first prepared by using a catalyst carrier selected from oxides and/or hydroxides and carrying thereon a zinc salt together with water soluble salt(s) of at least one element selected from the group consisting of the group 3A in periodic table by precipitation or impregnation. Then the precursor is calcined to thereby produce the catalytic composition. It is also possible to physically mixing and kneading at least one element selected from the group consisting of the elements of the group 3A in periodic table with a zinc compound to produce a dilute catalyst.

The water soluble salts to be used in the preparation of a catalytic composition precursor by the co-precipitation, impregnation or precipitation method can be used, so long as they are soluble in water. In general, zinc sulfate, zinc nitrate, zinc chloride, etc. may be exemplified as the examples of the zinc salt, while sulfates, nitrates, chlorides, etc. may be exemplified as the examples of the water soluble salt(s) of at least one element selected from the group consisting of the elements of the group 3A in periodic table. As the precipitation agent to be used for obtaining a catalytic composition precursor by the co-precipitation or precipitation method, aqueous solutions of alkalis such as ammonia, urea, ammonium carbonate, sodium carbonate, potassium hydroxide and sodium hydroxide. When the co-precipitation or precipitation method is employed, it is generally preferable to adjust the pH value of the solution to 2.0 to 10.5 in the step of the formation of the precipitate. Among these preparation methods, the co-precipitation method is particularly preferable.

The catalytic composition precursor thus obtained is decomposed into the oxide by calcination and then used as the catalytic composition of the present invention for producing an unsaturated alcohol. The catalytic composition precursor to be used in the present invention is decomposed into the oxide by calcining at a temperature of from 200° to 900° C., preferably from 300° to 700° C., though the present invention is not restricted thereto. When the calcining temperature is lower than 200° C., the activity cannot be fully achieved. When the calcining temperature exceeds 900° C., on the other hand, the surface area of the catalyst is decreased and thus the activity cannot be fully achieved.

The catalytic composition according to the present invention essentially consists of (a) zinc oxide and (b) oxide(s) of at least one metal selected from the group consisting of the elements of the group 3A in the periodic table. The composition ratio of (a)/(b) ranges from 1/0.01 to 1/1.2 (in terms of the weight of the oxide, the same will apply hereinafter). When the composition ratio is excluded from this range, the activity of the composition is largely lessened. The composition ratio (a)/(b) preferably ranges from 1/0.03 to 1/1.0, more preferably from 1/0.05 to 1/0.6. Within the scope of the present invention, the catalytic composition consisting of these components has a high activity and suffers from little formation of by-products such as hydrocarbons or ethers accompanying the hydrogenation. Moreover, it has been surprisingly found out that the unsaturated compound employed as the starting material is converted into the unsaturated alcohol while being scarcely accompanied by the isomerization of the cis-compound into the trans-compound with respect to the double bond therein.

In the catalytic composition according to the present invention, carrier(s) may be used so long as the weight ratio of (a) zinc oxide to (b) oxide(s) of metal(s) selected from the group consisting of the elements of the group 3A in the periodic table falls within the range as specified above. When carrier(s) are employed, the partial isomerization of the double bond in the starting unsaturated compound is observed exclusively in the case of a catalytic composition containing carrier(s) partly or entirely consisting of titanium and/or zirconium oxides. However, use of such a catalytic composition causes no problem, when its effect of achieving a high productivity is appreciated as superior, from an economical viewpoint, to the effect of regulating the isomerization. Namely, the effect achieved by the high activity thereof makes it advantageous. In addition, the catalytic composition may contain the third component such as a molding aid so long as the effects of the present invention are not worsened thereby, regardless of the use of carriers.

In the present invention, an unsaturated alcohol may be produced by a method selected from the suspended bed reaction system, the fluidized bed reaction system, the fixed bed reaction system, etc. In such a case, the catalyst is molded into a form suitable for the selected reaction system.

To produce an unsaturated alcohol in the present invention, the reaction conditions are selected in the following manner.

In the suspended bed reaction system or the fluidized bed reaction system, the catalyst is used preferably in an amount of from 5 to 30% by weight, more preferably from 5 to 20% by weight, based on the unsaturated fatty acid ester or triglyceride employed as the starting material. In order to shorten the reaction cycle time, however, it is preferable to perform the reaction at a high catalyst concentration. Although the reaction temperature preferably ranges from 150° to 350° C., more preferably from 240° to 320° C., a higher reaction temperature results in an increase in the hydrocarbons or ethers formed as the by-products. At a definite reaction rate, however, the isomerization of the double bond is scarcely influenced by temperature. The hydrogen pressure ranges preferably from 1 to 35 MPa, more preferably from 20 to 30 MPa. From the viewpoint of selectivity, it is preferable to perform the reaction under high pressure so as to achieve a high reaction rate within a short time of the contact of the reaction materials with the catalyst.

With respect to the introduction of the catalyst, the catalyst may be calcined in an oxidation or inert atmosphere, then fed in the form of an oxide and subjected to the reaction as such, regardless of the reaction system. Alternatively, the catalyst may be fed after appropriately pre-reduction processing under the above-mentioned conditions in, for example, the starting materials or the alcohol product, and then subjected to the reaction without causing any problem.

When an unsaturated alcohol is produced by the fixed bed reaction system, the catalyst is molded by a well-known method such as extrusion molding or tabletting. In the step of molding, pore-forming agents or lubricants may be added so long as the effects of the present invention are not worsened thereby. When a catalytic composition precursor is decomposed into an oxide by calcining, it may be decomposed by calcining in the form of a powder followed by molding. Alternatively, the uncalcined composition may be molded and then decomposed by calcining. The molded catalyst can be packed in a reactor and then subjected to the reaction as such. Alternatively, it may be preliminarily reduced in a reactor or out of the reaction system and then subjected to the reaction without causing any problem. Conditions for the reduction of the molded catalyst may be selected as follows. When performed in a gas phase, the reduction proceeds in a hydrogen atmosphere optionally diluted with an inert gas at a temperature of from 200° to 600° C. under atmospheric pressure to 35 MPa at a gas hourly space velocity (GHSV) of 0.1 to 10,000 l/hr. In addition, the above-mentioned reduction treatment may be carried out in the coexistence of the starting material and/or the alcohol product. When an unsaturated alcohol is produced by the fixed bed reaction system, it is preferable that the reaction temperature and the reaction pressure respectively ranges from 150° to 350° C. and from 1 MPa to 35 MPa. To establish a high productivity by suppressing the formation of the by-products such as hydrocarbons or ethers, it is more preferable that the reaction is performed at a temperature of from 240° to 320° C. under a pressure of from 20 to 30 MPa. The starting material is fed at a liquid hourly space velocity (LHSV) of from 0.1 to 2.0 l/hr.

Although it is preferable in the present invention to perform the reaction under elevated hydrogen pressure, the flow rate of the hydrogen gas fed into the fixed bed-type continuous reactor influences the reaction rate of the alcohol product. Thus, it is preferable to feed the hydrogen gas at a molar ratio of the hydrogen gas to the mole number of carbonyl groups in which the unsaturated fatty acid ester or triglyceride as the starting material have of 1:1 to 1:200. From the viewpoint of the reaction rate and economy it is more preferable that the molar ratio ranges from 1:2 to 1:100.

The starting material from which an unsaturated alcohol is produced in the present invention is an alkyl or alkenyl ester of an unsaturated fatty acid or a triglyceride having a long-chain aliphatic unsaturated hydrocarbon group.

As the alkyl or alkenyl ester of an unsaturated fatty acid, an alkyl or alkenyl ester of an unsaturated fatty acid having at least one double bond in its molecule may be used. As the alkyl or alkenyl group constituting this ester, linear or branched ones having 1 to 22 carbon atoms are preferable. Concrete examples thereof include methyl, ethyl, propyl, isopropyl, butyl, isobutyl, tert-butyl, hexyl, octyl, decyl and oleyl groups. Also, a mixture of alkyl or alkenyl esters of unsaturated fatty acids may be used without causing any problem. Such a mixture may further contain saturated fatty acid esters.

As the triglyceride having a long-chain aliphatic unsaturated hydrocarbon group, triglycerides of natural fats and oils having long-chain aliphatic unsaturated hydrocarbon groups (for example, beef tallow, coconut oil, palm oil, palm kernel oil, soybean oil, rapeseed oil) as such.

EXAMPLES

To further illustrate the present invention in greater detail, and not by way of limitation, the following examples are given.

Example 1
Preparation of Catalyst by Co-precipitation Method 89.25 g of zinc nitrate hexahydrate [$Zn(NO_3)_2 \cdot 6H_2O$] and 5.75 g of yttrium nitrate hexahydrate [$Y(NO_3)_3 \cdot 6H_2O$] were dissolved in 500 g of deionized water and heated to 90° C. under stirring. Into this aqueous solution was dropped 427.3 g of a 10% by weight aqueous solution of sodium carbonate over about 1 hour. The suspension thus formed was then subjected to heating-ripening for 1 hour while maintaining at 90° C. The precipitate thus obtained was separated by filtration, washed with 1.5 l of deionized water and dried at 110° C. over day and night. The catalytic composition precursor thus obtained was decomposed by calcining in the atmosphere at 420° C. for 2 hours to produce an unsaturated alcohol. The catalyst thus obtained was composed of 93.5 parts by weight of zinc oxide and 6.5 parts by weight of yttrium oxide ($ZnO/Y_2O_3=1/0.07$).
Production of Unsaturated Alcohol 150 g of methyl oleate [Exepal] M-OL (manufactured by Kao Corp.); saponification value (SV)=193, iodine value (IV)=84, hydroxyl value (OHV)=1.5] and 15 g of the calcined catalyst obtained by the above-mentioned method were fed into a rotary autoclave. Next, these materials, were heated from room temperature to 300° C. over about 30 minutes under a hydrogen pressure of 1 MPa at 900 r.p.m. When the temperature reached 300° C., the hydrogen pressure was elevated to 25 MPa and the reaction was performed for 240 minutes. After the completion of the reaction, the catalyst was eliminated by filtration and the oily matter was washed with water and dried to thereby prepare oleyl alcohol. The saponification value, hydroxyl value, iodine value and isomerization rate of the oleyl alcohol thus obtained were measured and thus the catalytic activity and selectivity were evaluated. The results are shown in Table 1.

The catalytic activity was evaluated by measuring the saponification value [SV (KOH-mg/g)] and hydroxyl value [OHV (KOH-mg/g)] of the alcohol product as the indication of the reactivity. A lower SV means the higher reaction rate of carbonyl group, while a higher OHV means the higher conversion rate into the alcohol. The selectivity was evaluated by measuring the iodine value [IV (I-g/100 g)] as the indication of the capability of maintaining double bond. A higher IV means the better capability of maintaining double bond. To examine the occurrence of the skeletal isomerization of double bond, the purity of the oleyl alcohol was determined by gas chromatography to the purity of the starting methyl oleate and the isomerization rate was calculated in accordance with the following formula. The isomerization rate was calculated at a definite reaction rate [i.e., saponification value (SV) of unsaturated alcohol product= 10] in the case of every catalyst.

<Formula for calculating the isomerization rate>

$$\text{Isomerization rate (\%)} = \left(1 - \frac{\text{purity of cis-9-octa-decenol in alcohol product}}{\text{purity of methyl cis-9-octa-decenoate in starting material.}}\right) \times 100$$

Example 2

A catalyst was prepared by the same method as in Example 1, except for using 148.7 g of zinc nitrate hexahydrate [$Zn(NO_3)_2 \cdot 6H_2O$], 14.36 g of yttrium nitrate hexahydrate [$Y(NO_3)_3 \cdot 6H_2O$] and 675.6 g of a 10% by weight aqueous solution of sodium carbonate. Next, oleyl alcohol was produced under the same reaction conditions as in Example 1. The catalyst employed herein was composed of 90.6 parts by weight of zinc oxide and 9.4 parts by weight of yttrium oxide ($ZnO/Y_2O_3=1/0.10$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 3

A catalyst was prepared by the same method as in Example 1, except for using 208.2 g of zinc nitrate hexahydrate [$Zn(NO_3)_2 \cdot 6H_2O$], 26.81 g of yttrium nitrate hexahydrate [$Y(NO_3)_3 \cdot 6H_2O$] and 1066.6 g of a 10% by weight aqueous solution of sodium carbonate. Next, oleyl alcohol was produced under the same reaction conditions as in Example 1. The catalyst employed herein was composed of 87.8 parts by weight of zinc oxide and 12.2 parts by weight of yttrium oxide ($ZnO/Y_2O_3=1/0.14$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 4

A catalyst was prepared by the same method as in Example 1, except for using 148.7 g of zinc nitrate hexahydrate [$Zn(NO_3)_2 \cdot 6H_2O$], 38.30 g of yttrium nitrate hexahydrate [$Y(NO_3)_3 \cdot 6H_2O$] and 861.3 g of a 10% by weight aqueous solution of sodium carbonate. Next, oleyl alcohol was produced under the same reaction conditions as in Example 1. The catalyst employed herein was composed of 78.3 parts by weight of zinc oxide and 21.7 parts by weight of yttrium oxide ($ZnO/Y_2O_3=1/0.10$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 5

A catalyst was prepared by the same method as in Example 1, except for using 89.25 g of zinc nitrate hexahydrate [$Zn(NO_3)_2 \cdot 6H_2O$], 34.47 g of yttrium nitrate hexahydrate [$Y(NO_3)_3 6H_2O$] and 576.4 g of a 10% by weight aqueous solution of sodium carbonate. Next, oleyl alcohol was produced under the same reaction conditions as in Example 1. The catalyst employed herein was composed of 70.6 parts by weight of zinc oxide and 29.4 parts by weight of yttrium oxide ($ZnO/Y_2O_3=1/0.42$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 6

A catalyst was prepared by the same method as in Example 1, except for using 89.25 g of zinc nitrate hexahydrate [$Zn(NO_3)_2 \cdot 6H_2O$], 12.99 g of lanthanum nitrate hexahydrate [$La(NO_3)_3 \cdot 6H_2O$] and 457.2 g of a 10% by weight aqueous solution of sodium carbonate. Next, oleyl alcohol was produced under the same reaction conditions as in Example 1. The catalyst employed herein was composed of 83.3 parts by weight of zinc oxide and 16.7 parts by weight of lanthanum oxide ($ZnO/La_2O_3=1/0.20$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 7

A catalyst was prepared by the same method as in Example 1, except for using 89.25 g of zinc nitrate hexahydrate [$Zn(NO_3)_2 \cdot 6H_2O$], 13.03 g of cerium nitrate hexahydrate [$Ce(NO_3)_3 \cdot 6H_2O$] and 457.2 g of a 10% by weight aqueous solution of sodium carbonate. Next, oleyl alcohol was produced under the same reaction conditions as in Example 1. The catalyst employed herein was composed of 83.2 parts by weight of zinc oxide and 16.8 parts by weight of cerium oxide ($ZnO/Ce_2O_3=1/0.20$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 8

A catalyst was prepared by the same method as in Example 1, except for using 89.25 g of zinc nitrate hexahydrate [$Zn(NO_3)_2 \cdot 6H_2O$], 15.24 g of thorium nitrate pentahydrate [$Th(NO_3)_3 \cdot 5H_2O$] and 457.2 g of a 10% by weight aqueous solution of sodium carbonate. Next, oleyl alcohol was produced under the same reaction conditions as in Example 1. The catalyst employed herein was composed of 76.1 parts by weight of zinc oxide and 23.9 parts by weight of thorium oxide ($ZnO/Th_2O_3=1/0.31$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Example 9

An unsaturated alcohol was produced under the same reaction conditions as in Example 1 by using the catalyst prepared in Example 3 and, as the starting material, deacidified palm kernel oil [saponification value (SV)=243, iodine value (IV)=17.3, acid value (AV)=0.8, hydroxyl value (OHV)=10.5].

The saponification value, hydroxyl value, iodine value and isomerization rate of the unsaturated alcohol thus obtained were measured and thus the catalytic activity and selectivity were evaluated by the same methods as in Example 1. The results are shown in Table 1.

Comparative Example 1

For comparison, a zinc oxide catalyst was prepared in the same method as in Example 1, except for using 89.25 g of zinc nitrate hexahydrate alone and 397.5 g of a 10% by weight aqueous solution of sodium carbonate. Next, oleyl alcohol was produced under the same reaction conditions as in Example 1.

The saponification value, hydroxyl value, iodine value and isomerization rate of the oleyl alcohol thus obtained were measured and thus the catalytic activity and selectivity were evaluated by the same methods as in Example 1. The results are shown in Table 1.

Comparative Example 2

For comparison, a catalyst was prepared by the same method as in Example 1, except for using 89.25 g of zinc nitrate hexahydrate [$Zn(NO_3)_2 \cdot 6H_2O$], 114.9 g of yttrium nitrate hexahydrate [$Y(NO_3)_3 \cdot 6H_2O$] and 993.8 g of a 10% by weight aqueous solution of sodium carbonate. Next, oleyl alcohol was produced under the same reaction conditions as in Example 1. The catalyst employed herein was composed of 41.9 parts by weight of zinc oxide and 58.1 parts by weight of yttrium oxide ($ZnO/Y_2O_3=1/1.39$).

The saponification value, hydroxyl value, iodine value and isomerization rate of the oleyl alcohol thus obtained were measured and thus the catalytic activity and selectivity were evaluated by the same methods as in Example 1. The results are shown in Table 1.

Comparative Example 3

For comparison, oleyl alcohol was produced under the same conditions as in Example 1, except for using a powdery zinc oxide/chromium oxide catalyst which was a commercially available catalyst for producing unsaturated alcohols (manufactured by Engelhard Corp.).

The saponification value, hydroxyl value, iodine value and isomerization rate of the oleyl alcohol thus obtained were measured and thus the catalytic activity and selectivity were evaluated by the same methods as in Example 1. The results are shown in Table 1.

TABLE 1

| Example No./ Comparative Example No. | Analytical data of unsaturated alcohol | | | |
|---|---|---|---|---|
| | SV | OHV | IV | Isomerization rate (%) |
| Example 1 | 11.2 | 191.1 | 90.2 | 4.0 |
| Example 2 | 9.8 | 195.7 | 89.8 | 3.8 |
| Example 3 | 4.6 | 198.4 | 87.8 | 3.7 |
| Example 4 | 5.1 | 197.2 | 87.5 | 3.8 |
| Example 5 | 13.5 | 186.0 | 90.5 | 4.2 |
| Example 6 | 10.4 | 191.9 | 91.2 | 4.0 |
| Example 7 | 11.3 | 192.0 | 90.8 | 4.1 |
| Example 8 | 4.0 | 198.9 | 88.0 | 3.7 |
| Example 9 | 11.0 | 232.3 | 18.4 | 3.9 |
| Comparative Example 1 | 61.0 | 90.2 | 93.5 | 41.2 |
| Comparative Example 2 | 89.3 | 61.2 | 89.0 | 44.4 |
| Comparative Example 3 | 64.2 | 88.7 | 93.9 | 37.0 |

As is apparent from the result of Table 1, the samples of the present invention give higher reaction rates and conversion rates, better capability of maintaining double bond and lower isomerization rates, as compared with those of the comparative examples.

Example 10

As a carrier, 50.0 g of commercially available titanium oxide (manufactured by Sakai Kagaku K.K.) was suspended in 500 g of deionized water and then mixed with an aqueous solution prepared by dissolving 29.75 of zinc nitrate hexahydrate [$Zn(NO_3)_2 \cdot 6H_2O$] and 7.66 g of yttrium nitrate hexahydrate [$Y(NO_3)_3 \cdot 6H_2O$] in 500 g of deionized water to thereby obtain a suspension. Next, this suspension was heated to 90° C. while stirring. Then 172.3 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and calcined in the atmosphere at 420° C. for 2 hours to thereby obtain a catalyst. The catalyst thus obtained was composed of 13.5 parts by weight of zinc oxide, 3.7 parts by weight of yttrium oxide ($ZnO/Y_2O_3=1/0.27$) and 82.8 parts by weight of titanium oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

Example 11

As a carrier, 50.0 g of commercially available titanium oxide (manufactured by Sakai Kagaku K.K.) was suspended in 500 g of deionized water and then mixed with an aqueous solution prepared by dissolving 29.75 of zinc nitrate hexahydrate [$Zn(NO_3)_2 \cdot 6H_2O$] and 21.65 g of lanthanum nitrate hexahydrate [$La(NO_3)_3 \cdot 6H_2O$] in 500 g of deionized water to thereby obtain a suspension. Next, this suspension was heated to 90° C. while stirring. Then 231.9 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and calcined in the atmosphere at 420° C. for 2 hours to thereby obtain a catalyst. The catalyst thus obtained was composed of 12.3 parts by weight of zinc oxide, 12.3 parts by weight of lanthanum oxide ($ZnO/La_2O_3=1/1.0$) and 75.4 parts by weight of titanium oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

Example 12

As a carrier, 50.0 g of commercially available titanium oxide (manufactured by Sakai Kagaku K.K.) was suspended in 500 g of deionized water and then mixed with an aqueous solution prepared by dissolving 29.75 of zinc nitrate hexahydrate [$Zn(NO_3)_2 \cdot 6H_2O$] and 21.71 g of cerium nitrate hexahydrate [$Ce(NO_3)_3 \cdot 6H_2O$] in 500 g of deionized water to thereby obtain a suspension. Next, this suspension was heated to 90° C. under stirring. Then 231.9 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and calcined in the atmosphere at 420° C. for 2 hours to thereby obtain a catalyst. The catalyst thus obtained was composed of 12.3 parts by weight of zinc oxide, 12.3 parts by weight of cerium oxide ($ZnO/Ce_2O_3=1/1.0$) and 75.4 parts by weight of titanium oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

Example 13

As a carrier, 39.1 g of commercially available aluminum oxide (manufactured by Mizusawa Kagaku K.K.) was suspended in 500 g of deionized water and then mixed with an aqueous solution prepared by dissolving 119.0 g of zinc nitrate hexahydrate [$Zn(NO_3)_2 \cdot 6H_2O$] and 15.32 g of yttrium nitrate hexahydrate [$Y(NO_3)_3 \cdot 6H_2O$] in 500 g of deionized water to thereby obtain a suspension. Next, this suspension was heated to 90° C. while stirring. Then 609.5 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and calcined in the atmosphere at 420° C. for 2 hours to thereby obtain a catalyst. The catalyst thus obtained was composed of 42.7 parts by weight of zinc oxide, 5.9 parts by weight of yttrium oxide ($ZnO/Y_2O_3=1/0.14$) and 51.3 parts by weight of aluminum oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

Example 14

As a carrier, 39.1 g of commercially available aluminum oxide (manufactured by Mizusawa Kagaku K.K.) was suspended in 500 g of deionized water and then mixed with an aqueous solution prepared by dissolving 119.0 g of zinc nitrate hexahydrate [$Zn(NO_3)_2 \cdot 6H_2O$] and 17.32 g of lanthanum nitrate hexahydrate [$La(NO_3)_3 \cdot 6H_2O$] in 500 g of deionized water to thereby obtain a suspension. Next, this suspension was heated to 90° C. under stirring. 609.5 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and calcined in the atmosphere at 420° C. for 2 hours to thereby obtain a catalyst. The catalyst thus obtained was composed of 41.7 parts by weight of zinc oxide, 8.3 parts by weight of lanthanum oxide ($ZnO/La_2O_3$=1/0.20) and 50.0 parts by weight of aluminum oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

Example 15

As a carrier, 35.0 g of commercially available aluminum oxide/magnesium oxide (manufactured by Kyowa Kagaku K.K.; Kyowaad) was suspended in 500 g of deionized water and then mixed with an aqueous solution prepared by dissolving 59.50 g of zinc nitrate hexahydrate [$Zn(NO_3)_2 \cdot 6H_2O$] and 15.32 g of yttrium nitrate hexahydrate [$Y(NO_3)_3 \cdot 6H_2O$] in 500 g of deionized water to thereby obtain a suspension. Next, this suspension was heated to 90° C. under stirring. Then 344.5 g of a 10% by weight aqueous solution of sodium carbonate was dropped thereinto over about 1 hour. After the completion of the addition, the suspension was subjected to heating-ripening for 1 hour while maintaining at 90° C. The precipitate thus obtained was separated by filtration and washed with 3 liter of deionized water. Then it was dried at 110° C. over day and night and baked in the atmosphere at 420° C. for 2 hours to thereby obtain a catalyst. The catalyst thus obtained was composed of 33.4 parts by weight of zinc oxide, 9.3 parts by weight of yttrium oxide ($ZnO/Y_2O_3$=1/0.28) and 28.9 parts by weight of aluminum oxide/magnesium oxide.

By using this catalyst, oleyl alcohol was produced under the same conditions as in Example 1. The saponification value, hydroxyl value, iodine value and isomerization rate of the oleyl alcohol thus obtained were measured and thus the catalytic activity and selectivity were evaluated by the same methods as in Example 1. The results are shown in Table 2.

TABLE 2

| Example No./ Comparative Example No. | Analytical data of unsaturated alcohol | | | |
|---|---|---|---|---|
| | SV | OHV | IV | Isomerization rate (%) |
| Example 10 | 5.6 | 190.9 | 90.1 | 24.5 |
| Example 11 | 7.8 | 190.8 | 92.8 | 23.1 |
| Example 12 | 11.2 | 189.6 | 91.9 | 24.3 |
| Example 13 | 15.3 | 180.7 | 91.3 | 4.3 |
| Example 14 | 18.9 | 168.1 | 90.0 | 5.0 |
| Example 15 | 27.7 | 161.3 | 92.5 | 5.5 |

Example 16

To the uncalcined powdery catalyst prepared in Example 3 were added as binder components sodium carboxymethylcellulose and alumina. Then the obtained mixture was processed into molded articles (3 mm in diameter, 3 mm in height) with use of a tabletting machine. These molded articles were calcined in the atmosphere at 420° C. for 2 hours to thereby obtain a molded catalyst. 15 g of this molded catalyst was fed into a rotary autoclave provided with a basket for supporting the catalyst. By using methyl oleate [Exepal M-OL (manufactured by Kao); saponification value (SV)=193, iodine value (IV)=84, hydroxyl value (OHV)=1.5] as the starting material, the reaction was performed at a temperature of 300° C. under a hydrogen pressure of 25 MPa for 8 hours. After the completion of the reaction, the oily matter alone was taken up, washed with water and dried to thereby obtain oleyl alcohol. The molded catalyst was subjected as such to the subsequent reaction. This reaction procedure was repeated thrice and the oleyl alcohol obtained each time was analyzed so as to evaluate its catalytic activity and selectivity in the same manner as in Example 1. The results are shown in Table 3.

Comparative Example 4

For comparison, the same reaction procedure for obtaining oleyl alcohol as in Example 16 was repeated thrice, except for using a molded zinc oxide/chromium oxide catalyst (3 mm in diameter, 3 mm in height) which was a commercially available catalyst for producing unsaturated alcohols (manufactured by Engelhard Corp.). Then the oleyl alcohol obtained each time was analyzed so as to evaluate its catalytic activity and selectivity in the same manner as in Example 1. The results are shown in Table 3.

Comparative Example 5

For comparison, sodium carbonate was dropped as a precipitation agent into an aqueous solution containing 11.0 g of zinc nitrate hexahydrate, ferric sulfate [$Fe_2(SO_4)_3$, content=0%) and 6.5 g of zirconium nitrate dihydrate to thereby obtain a three-component precipitate of iron/zinc/zirconium. The powder obtained by drying this precipitate was tabletted and decomposed by calcining in the same manner as in Example 16 to thereby obtain a molded catlyst. By using the molded catalyst thus obtained, the same reaction procedure for obtaining oleyl alcohol as in Example 16 was repeated thrice. Then the oleyl alcohol obtained each time was analyzed so as to evaluate its catalytic activity and selectivity in the same manner as in Example 1. The results are shown in Table 3.

TABLE 3

| Example No./ Comparative Example No. | Reaction No. | Analytical data of oleyl alcohol | | | |
|---|---|---|---|---|---|
| | | SV | OHV | IV | Isomerization rate (%) |
| Example 16 | 1 | 7.0 | 193.2 | 89.1 | 6.3 |
| | 2 | 9.4 | 192.0 | 90.2 | 6.5 |
| | 3 | 11.8 | 190.6 | 90.8 | 6.4 |
| Comparative Example 4 | 1 | 78.1 | 90.2 | 92.4 | 38.7 |
| | 2 | 80.3 | 86.6 | 92.6 | 38.5 |
| | 3 | 79.7 | 88.2 | 92.3 | 39.0 |
| Comparative Example 5 | 1 | 6.9 | 191.3 | 90.8 | 7.9 |
| | 2 | 6.7 | 192.5 | 73.5 | 24.3 |
| | 3 | 7.4 | 190.7 | 52.1 | 52.1 |

As is apparent from the results of Table 3, the catalysts of the present invention are excellent in catalytic activity and selectivity and can sustain these characteristics even after repeated use.

While the invention has been described in detail and with reference to specific embodiments thereof, it will be apparent to one skilled in the art that various changes and modifications can be made therein without departing from the spirit and scope thereof.

What is claimed is:

1. A process for producing an unsaturated alcohol which comprises hydrogenating an alkyl or alkenyl ester of an unsaturated fatty acid or a triglyceride having a long-chain aliphatic unsaturated hydrocarbon group in the presence of a catalytic composition which is a composite metal oxide consisting of (a) zinc oxide and (b) oxide(s) of at least one metal selected from the group consisting of the elements of the group 3A in the periodic table and having a weight ratio of (a)/ from 1/0.01 to 1/1.2.

2. A process for producing an unsaturated alcohol as claimed in claim 1, wherein the hydrogen pressure is from 1 MPa to 35 MPa.

3. A process for producing an unsaturated alcohol as claimed in claim 1, wherein the element of the group 3A in the periodic table is Y, La, Ce or Th.

4. A process for producing an unsaturated alcohol as claimed in claim 1, wherein the reaction temperature is from 150° to 350° C.

* * * * *

UNITED STATES PATENT AND TRADEMARK OFFICE
CERTIFICATE OF CORRECTION

PATENT NO.   : 5,817,892
DATED        : October 6, 1998
INVENTOR(S)  : Hiroyuki TAMURA, et al.

It is certified that error appears in the above-identified patent and that said Letters Patent is hereby corrected as shown below:

On the title page, Item [30], the Foreign Application Priority Data, is incorrect. It should be:

--Sep. 6, 1996    [JP]   Japan............8-236219--

Signed and Sealed this

Eighteenth Day of May, 1999

Attest:

Q. TODD DICKINSON

Attesting Officer

Acting Commissioner of Patents and Trademarks